United States Patent
Kotzev

[11] Patent Number: 5,874,044
[45] Date of Patent: Feb. 23, 1999

[54] HEAT STERILIZATION OF CYANOACRYLATE

[76] Inventor: Dimiter Lubomirov Kotzev, 21 Carron Close, Corby, Northants NN17 2LB, United Kingdom

[21] Appl. No.: 740,405

[22] Filed: Oct. 29, 1996

[30] Foreign Application Priority Data

Nov. 2, 1995 [GB] United Kingdom .................... 9522435

[51] Int. Cl.$^6$ .................................................... B01J 19/00
[52] U.S. Cl. ............................................................ 422/40
[58] Field of Search ..................... 422/1, 40, 22; 7/10

[56] References Cited

U.S. PATENT DOCUMENTS

| | | | |
|---|---|---|---|
| 2,912,454 | 11/1959 | McKeever et al. | 588/372 |
| 3,360,124 | 12/1967 | Stonehill | 206/524.1 |
| 3,527,841 | 9/1970 | Wicker, Jr. et al. | 528/354 |
| 5,436,363 | 7/1995 | Wang et al. | 558/381 |
| 5,530,037 | 6/1996 | McDonnell et al. | 522/79 |
| 5,649,648 | 7/1997 | Lier et al. | 222/206 |

*Primary Examiner*—Robert Warden
*Assistant Examiner*—Alex Noguerola
*Attorney, Agent, or Firm*—Baker & Botts, LLP

[57] ABSTRACT

Cyanoacrylate preparations for medical and surgical applications are sterilized by heating in a suitable container at a temperature of at least 160° C. The preferred container is a squeezable aluminum tube and the preferred temperature is above 170° C. Cyanoacrylate adhesive compositions sterilized by heat have improved shelf life compared to those sterilized by ionizing radiation.

14 Claims, No Drawings

HEAT STERILIZATION OF CYANOACRYLATE

BACKGROUND OF THE INVENTION

1. Field of the Invention

The present invention relates to cyanoacrylate preparations and, more particularly, to the sterilization of cyanoacrylate preparations for use in medical or surgical procedures and to sterilized cyanoacrylate packages.

2. Brief Description of the Background

It is known to use 2-cyanoacrylate esters for bonding tissue in medical or surgical procedures performed upon the human or animal body. 2-cyanoacrylate esters polymerize rapidly, and often instantaneously, upon contact with tissue or fluid. The cyanoacrylate polymer is thereafter degraded, metabolized and removed from the body.

In order to be used for medical, including surgical, purposes, 2-cyanoacrylate ester preparations must be sterilized.

It is known to sterilize 2-cyanoacrylate preparations by the use of heat or of radiation. Both techniques tend to cause polymerization of the cyanoacrylate monomer, or at least tend to reduce the shelf life. There therefore remains a demand in the market place for sterilized 2-cyanoacrylate adhesive compositions which have a good shelf life.

It is believed that sterile 2-cyanoacrylate preparations now on the market have, in the main, been sterilized by the use of ionizing radiation. Whilst ionizing radiation has, therefore, apparently been perceived as the preferred method of sterilization, there is a substantial capital cost associated with this procedure and it necessitates the careful use of dosimetry procedures. The biological effects of radiation can also create their own problems.

Cyanoacrylate monomer must be packaged in an inert and adequately water-resistant container, since atmospheric moisture causes polymerization. Aluminum containers, and more particularly tubes, are sometimes used for cyanoacrylate sold for industrial or commercial purposes.

Polyolefin has been the material of choice for commercial medical-grade cyanoacrylate. Polyolefin containers however are permeable to atmospheric moisture the ingress of which into the container detrimentally affects the properties and shelf life of the stored cyanoacrylate. As already stated, both heat and ionizing radiation tend to cause or promote polymerization of 2-cyanoacrylate monomer, at least to the extent of reducing shelf life and, accordingly, sterile cyanoacrylate requires a container which will not promote or cause polymerization during the sterilization process. Aluminum has not found favour as a container for sterile cyanoacrylate.

SUMMARY OF THE INVENTION

The present invention overcomes the problems and disadvantages associated with current strategies and designs and provides a novel method of sterilizing a 2-cyanoacrylate ester preparation. The method contradicts known teaching as to the stability of cyanoacrylate and yet enables production of a product of outstanding stability. The invention also provides a novel sterile 2-cyanoacrylate ester preparation and a novel package containing sterile cyanoacrylate. Other embodiments and advantages of the invention are set forth, in part, in the description which follows and, in part, will be obvious from this description or may be learned from the practice of the invention.

DESCRIPTION OF THE INVENTION

As embodied and broadly described herein, the present invention is directed to methods for sterilizing cyanoacrylate preparations and to the resulting sterile preparations.

The Method

In one aspect the invention provides a method of sterilizing a 2-cyanoacrylate ester preparation, comprising heating the preparation to a temperature of at least 160° C. The prior art teaches that cyanoacrylate polymerizes at a temperature of 160° C. (U.S. Pat. No. 3,360,124). The sterilization method is preferably formed at a temperature of at least 170° C. and more preferably at a temperature of about 180° C., or more.

The British Pharmacopoeia recommends heating at a minimum of 160° C. for not less than 2 hours, a minimum of 170° C. for not less than 1 hour and a minimum of 180° C. for not less than 30 minutes for effective sterilization. In accordance with the present invention, the 2-cyanoacrylate ester preparations are preferably heated for a period of time in accordance with the recommendations of the British Pharmacopoeia. It is most preferred that the cyanoacrylate preparation is maintained at a temperature of about 180° C. for at least 30 minutes, and more preferably for about 45 minutes. Such processes have, against all expectations, been found capable of resulting in a product which not only equals the stability of prior art sterile cyanoacrylate preparations but exceeds the stability of such preparations by a considerable margin.

Thus it has surprisingly been found that when the method of the invention is performed upon 2-cyanoacrylate ester preparations contained in an aluminum container, it is possible for the sterilized cyanoacrylate to retain its fluidity for a period in excess of 220 days at 55° C.

This compares with fluidity retention periods at 55° C. of 4 days and 6 days for two sterile cyanoacrylate products on the market. The method of the invention is therefore preferably performed upon a sealed aluminum container, although alternative thermally stable containers may be used. A particularly preferred container is an aluminum tube, e.g. a tightly crimped aluminum tube.

The method of the invention is not restricted as to the method of heating but dry heat sterilization is preferred. In an exemplary procedure, closed containers of cyanoacrylate preparation are placed in a dry heat sterilizer pre-heated to 180° C. The sterilizer temperature is allowed to return to 180° C. and the containers are held in the sterilizer for a period of at least 30 minutes and more normally of up to 45 minutes.

The Preparation

The method of the invention may be applied in principle to any 2-cyanoacrylate ester The cyanoacrylate is preferably an aliphatic 2-cyanoacrylate ester and preferably an alkyl, cycloalkyl, alkenyl or alkoxyalkyl 2-cyanoacrylate ester. The alkyl group may have from 1 to 16 carbon atoms and is more preferably a $C_1$–$C_8$ alkyl ester and most preferably a $C_1$–$C_4$ alkyl ester. Suitable esters include the methyl, ethyl, n-propyl, isopropyl, n-butyl, isobutyl, pentyl, hexyl, cyclohexyl, heptyl, octyl, 2-methoxyethyl and 2- ethoxyethyl esters of cyanoacrylic acid.

The cyanoacrylate preparation will contain any additives necessary to impart the desired properties to the preparation as viscosity, color, X-ray opacity, etc. Commercial medical cyanoacrylate preparations contain one or more additives to prevent premature polymerization. Usually, cyanoacrylate monomers are stabilized with anionic and free-radical polymerization inhibitors. Anionic polymerization inhibitors known in the art include soluble acidic gases (for example sulphur dioxide), and phosphoric, carboxylic and organic sulfonic acids. Free-radical polymerization inhibitors include hydroquinone, t-butyl catechol, hydroxyanisole, butylated hydroxyanisole and butylated hydroxytoluene.

The Package

The heat-sterilized cyanoacrylate preparations of the invention may be packaged in a container made of any suitable material. In this respect, the container must be heat-resistant up to the sterilization temperature, present an adequate barrier to atmospheric moisture and be cyanoacrylate-compatible. Materials meeting these requirements include metal and glass. A particularly preferred material is aluminum, especially aluminum formed into a squeezable tube. Preferred aluminum tubes comprise a nozzle which is hermetically sealed by a piercable membrane of aluminum and are filled at their end remote from the nozzle prior to closure of the open end by tight crimping. In the result, therefore, preferred embodiments of the invention reside in a substantially hermetically sealed aluminum container, e.g. an aluminum tube, containing a sterile 2-cyanoacrylate ester preparation.

The present invention enables provision of 2-cyanoacrylate ester preparations which retain their fluidity at 55° C. for a prolonged period when in a sealed aluminum container. Preferred preparations are capable of retaining their fluidity at 55° C. for a period of at least 50 days when in a sealed aluminum container, and more preferably for a period of at least 100 days. Particularly preferred preparations are capable of retaining their fluidity at 55° C. for a period of at least 200 days, e.g. 220 days or more. As measured in this way, the invention enables provision of sterile adhesive having a stability in excess of 36 times that of two products currently on the market.

The following experiments are offered to illustrate embodiments of the invention, and shall not be viewed as limiting the scope of the invention.

EXAMPLE

A preparation was made of n-butyl 2-cyanoacrylate (NBCA) stabilized with 100 ppm $SO_2$ and 1000 ppm butylated hydroxyanisole. The preparation was placed into aluminum tubes and sterilized by ionizing radiation ($\gamma$ and electron beam radiation) and by heating. The stabilities of the resultant products were compared with each other and with the stabilities of two commercially available medical grade cyanoacrylates. The ability of the preparations to polymerize promptly upon application to tissue was checked by ascertaining polymerization time on bovine plasma.

1. Sterilization procedures:

NBCA was filled into aluminum tubes, which were hermetically closed by tight crimping.

a. Dry heat sterilization: The tubes are placed in a preheated, validated dry heat sterilizer. The tubes are kept for 45 minutes once the temperature levels at 180° C. (The theoretical sterilization time at this temperature is 9 minutes. The recommended sterilization cycle in *British Pharmacopoeia* (p.A197, Vol II, Ed. 1993) is 30 minutes at 180° C.)

b. Ionizing radiation: The tubes were placed in validated ionization chambers where they received the prescribed dose of 25kGy (*British Pharmacopoeia*, p.A198, Vol II, Ed. 1993) of $\gamma$ or e beam exposure.

2. Polymerization time on bovine plasma:

Freshly reconstituted bovine plasma in a suitable container is placed and equilibrated in a water bath at 37° C. Using a 27 Gauge needle a drop of NBCA is dropped on the plasma surface from a distance of 2 cm, The time interval from the moment the drop hits the surface to the moment it polymerizes (looses transparency) is measured with a stopwatch.

3. Stability at 55° C.:

Aluminum tubes containing NBCA prior to and following sterilization are placed at a constant temperature of 55° C. and monitored daily for fluidity of the cyanoacrylate by shaking. The number of days with retained fluidity is recorded. This is a widely practiced accelerated stability test for cyanoacrylate adhesives relating to their shelf-life. The results are shown in Tables 1 and 2 below.

TABLE 1

Properties of NBCA following different sterilization treatments

| No. | Sterilization method | Sterilization details | Polymerization time on bovine plasma | Color | Viscosity increase after sterilization | Stability at 55° C. (days) |
|---|---|---|---|---|---|---|
| 1 | none | — | instant | APHA 100 | — | >220 |
| 2 | $\gamma$ | 25kGy | instant | Gardner 5 | yes | 12 |
| 3 | e beam | 25kGy | instant | APHA 300 | yes | 36 |
| 4 | dry heat | 45 mins at 180° C. | instant | APHA 200 | no | >220 |

TABLE 2

Comparison of properties of NBCA medical adhesives

| NBCA | Sterilization method | Polymerization time on bovine plasma | Appearance | Stability at 55° C. (days) |
|---|---|---|---|---|
| Competitor No 1 | unknown | instant | intentionally colored blue | 4 |
| Competitor No 2 | $\gamma$-radiation | 2 seconds | clear, APHA 100 | 6 |
| Product #4 of Table 1 | dry heat | instant | clear, APHA 200 | >220 |

Other embodiments and cases of the invention will be apparent for those skilled in the art from consideration of the specification and practice of the invention disclosed herein. All U.S. patents and other documents referred herein, for whatever reason, are specifically incorporated by reference. It is intended that the specification and examples be considered exemplary only, with the true scope and spirit of the invention being indicated by the following claims.

I claim:

1. A method of sterilizing a 2-cyanoacrylate preparation that consists of only a 2-cyanoacrylate compound and one or more anionic or free-radical polymerization inhibitors that prevent premature polymerization, the method comprising heating said preparation in a suitable container that is hermetically closed to a temperature of at least 160° C. without causing polymerization of the 2-cyanoacrylate preparation.

2. A method of claim 1 wherein the preparation is heated to a temperature of at least 170° C.

3. A method of claim 2 wherein the preparation is heated to a temperature of about 180° C.

4. A method of claim 3 wherein the preparation is maintained at a temperature of about 180° C. for at least 30 minutes.

5. A method of claim 4 wherein the preparation is maintained at a temperature of about 180° C. for about 45 minutes.

6. A method of claim 1 wherein the preparation is contained in an aluminum container during performance of said heating.

7. A method of claim 1 wherein the preparation is an alkyl, cycloalkyl, alkenyl or alkoxyalkyl 2-cyanoacrylate preparation.

8. A method of claim 7 wherein the preparation is a $C_1$–$C_4$ alkyl 2-cyanoacrylate preparation.

9. A method of claim 8 wherein the preparation is an n-butyl 2-cyanoacrylate preparation.

10. The method of claim 1 wherein the one or more anionic or free-radical polymerization inhibitors comprise sulphur dioxide and butylated hydroxy anisole.

11. A method of claim 1 wherein the 2-cyanoacrylate ester compound is a 2-cyanoacrylate ester.

12. A method of claim 1 wherein the 2-cyanoacrylate compound is an aliphatic 2-cyanoacrylate ester.

13. A method of sterilizing a 2-cyanoacrylate preparation consisting of one or more anionic or free-radical polymerization inhibitors that prevent premature polymerization, comprising heating the preparation in an aluminum container to a temperature of at least 170° C., the sterilized preparation retaining its fluidity for a period of at least 50 days when in a sealed aluminum container.

14. A composition comprising a 2-cyanoacrylate ester preparation sterilized by the method of claim 13.

* * * * *